United States Patent [19]
Shi et al.

[11] Patent Number: 6,054,302
[45] Date of Patent: *Apr. 25, 2000

[54] HIGH SOLIDS, SINGLE PHASE PROCESS FOR PREPARING ENZYME-CONVERTED STARCHES

[75] Inventors: Yong-Cheng Shi, Somerville; James L. Eden, Millstone; James J. Kasica, Whitehouse St.; Roger Jeffcoat, Bridgewater, all of N.J.

[73] Assignee: National Starch and Chemical Investment Holding Corporation, Wilmington, Del.

[*] Notice: This patent issued on a continued prosecution application filed under 37 CFR 1.53(d), and is subject to the twenty year patent term provisions of 35 U.S.C. 154(a)(2).

[21] Appl. No.: 08/643,719

[22] Filed: May 6, 1996

[51] Int. Cl.$^7$ ...................................................... C12P 19/22
[52] U.S. Cl. ................................ 435/95; 435/96; 435/98; 435/99; 435/101; 435/161; 435/165
[58] Field of Search .................................. 435/95, 96, 98, 435/99, 101, 161, 165

[56] References Cited

U.S. PATENT DOCUMENTS

| | | | |
|---|---|---|---|
| 2,808,381 | 10/1957 | Stone | 260/17.4 |
| 4,643,894 | 2/1987 | Porter et al. | 424/35 |
| 4,725,441 | 2/1988 | Porter et al. | 424/479 |
| 4,828,841 | 5/1989 | Porter et al. | 424/479 |
| 5,565,509 | 10/1996 | Nguyen et al. | 524/47 |

FOREIGN PATENT DOCUMENTS 1 406 508  9/1975  United Kingdom.

*Primary Examiner*—Donna C. Wortman
*Assistant Examiner*—Mary K Zeman
*Attorney, Agent, or Firm*—Karen G. Kaiser

[57] ABSTRACT

A high solids, enzyme conversion process for preparing an enzyme-converted starch is carried out by adding to a modified or unmodified starch, preferably a granular starch, water and an enzyme in an amount sufficient to produce a single phase powdered mixture without a visible free water phase. The enzyme is activated by heating while maintaining a substantially constant moisture content in the mixture. The enzyme converted starch is recovered as a syrup, a granular converted starch, or mixtures thereof, or as a powder obtained by drying the syrup.

24 Claims, 5 Drawing Sheets

HIGH SOLIDS, SINGLE PHASE PROCESS FOR PREPARING ENZYME-CONVERTED STARCHES

BACKGROUND OF THE INVENTION

Enzyme conversions are typically carried out in a batch or continuous aqueous slurry process. Typically, a "high solids" enzyme slurry contains about 18–35 wt. % solids. The conversion is carried out as the granular starch is being heated (to gelatinize it) so that the high viscosity of the native starch is not reached and agitation can be maintained in the high solids mixture. After the enzyme conversion is completed, the enzyme is inactivated. The converted starch is often diluted prior to use.

Some of the patents covering enzyme conversion or acid and enzyme conversion are discussed below.

U.S. Pat. No. 2,609,326 (issued Sep. 2, 1952 to W. W. Pigman et al.) discloses rapidly gelatinizing and dispersing starch granules in hot water while subjecting the starch to intense agitation and shearing, immediately converting the gelatinized and dispersed starch at an elevated temperature with a starch-liquefying amylase characterized by its ability to hydrolyze the starch molecules into large fragments, inactivating the enzyme, and immediately drying the enzyme converted starch.

U.S. Pat. No. 3,560,343 (issued Feb. 2, 1971 to F. C. Armbruster et al.) discloses a process where a starch is acid hydrolyzed to a D.E. less than 15 and then converted with a bacterial alpha amylase to a DE between 10 and 25.

Japanese 46-14706 (published Apr. 20, 1971) discloses a continuous process for preparing a granular converted starch which swells, but does not dissolve in cold water, and which is reduced in viscosity. A starch alpha amylase mixture having a water content of 40–60%, containing buffer to adjust the pH to 5–7, is cured for several hours at room temperature, or a temperature at or below the gelatinization temperature, after which it is put into a starch dryer maintained at 70–150° C. During the drying, the temperature and water content change to those suitable for hydrolyzing the starch. The hydrolysis, drying of the hydrolyzed starch, and deactivation of the residual enzyme simultaneously occur during the heating at 70–150° C. A liquefaction-type amylase shows the strongest hydrolytic activity at 70–90° C., but at higher temperatures (i.e., above 90° C.), if the moisture content is above 35%, the starch undergoes the hydrolytic activity but is gelatinized at the same time and if the water content of the mixture is less than 30%, it becomes more difficult to gelatinize the starch, but at the same time the hydrolysis by the enzyme shows a tendency to fall off rapidly. To satisfy these opposing tendencies, it is necessary to reduce the water content of the mixture from 40–60% to 30–35% in the dryer and to increase the temperature to 90–100° C. during the enzyme hydrolysis.

U.S. Pat. No. 3,663,369 (issued May 16, 1972 to A. L. Morehouse et al.) discloses a two-stage hydrolysis. The first stage is carried out with acids or enzymes at elevated temperatures for short periods to liquify the starch with very little dextrinization or saccharification. The second stage is carried out at an alkaline pH with bacterial alpha amylase to achieve the desired D.E.

U.S. Pat. No. 3,644,126 (issued Feb. 22, 1972 to D. A. Bodnar) discloses a two step of making a starch conversion syrup by treating an aqueous slurry of starch with a starch-liquefying enzyme under conditions sufficient to give a product with a D.E. of <35. The liquefied starch slurry is then digested with glucoamylase and malt enzymes to obtain a syrup having <45% dextrose and sufficient maltose to provide at 85% total fermentable sugars.

U.S. Pat. No. 3,849,194 (issued Nov. 19, 1974 to F. C. Armbruster) discloses treating a waxy starch with a bacterial alpha amylase at a temperature above 85° C. to liquify the waxy starch, cooling the liquified waxy starch to about 80° C., and converting the liquified waxy starch with the bacterial alpha amylase to a D.E. of from about 5 to about 25.

U.S. Pat. No. 3,853,706 (issued Dec. 10, 1974 to F. C. Armbruster) discloses hydrolyzing starch with a bacterial alpha amylase to a DE of less than 15, terminating the hydrolysis by heat treatment, and further converting to a DE of between about 5 and 20.

U.S. Pat. No. 3,922,196 (issued Nov. 25, 1975 to H. W. Leach) discloses hydrolyzing an aqueous slurry of starch (5 to about 40% solids) with alpha amylase and optionally a saccharifying enzyme (e.g., beta amylase or glucoamylase). The saccharifying enzyme is preferably added after the granular starch is substantially solubilized at the solubilization temperature or a lower temperature (e.g., 50–65° C. and pH 4–6). The mixture is heated at a temperature between the initial gelatinization temperature and the actual gelatinization temperature of the starch, preferably at a pH of 5–7.

U.S. Pat. No. 4,014,743 (issued Mar. 29, 1977 to W. C. Black) discloses a method for the continuous enzyme liquefication of starch. Preferably, the starch is a raw starch. A suitable enzyme is bacterial alpha amylase. An enzyme-containing suspension of the starch (10–45 wt. % on a dry solids basis) is continuously added to an agitated body of the heated converted starch (170–210° F.). The incoming starch is gelatinized and mixed with the partially converted starch to maintain a blend having a viscosity low enough to be readily agitated and pumped. A stream of the blend is continuously removed from the conversion tank and treated to inactivate the enzyme. The process is controlled to limit the maximum viscosity of the blend to a Brookfield viscosity of not over 5000 cps (100 rpm and 88° C.–190° F.). A blend of starches that have been subjected to different degrees of enzyme conversion is obtained since the heating and enzyme treatment is not uniform for the individual starch granules or molecules.

U.K. 1,406,508 (published Sep. 17, 1975) discloses a continuous process for liquefying natural or chemically modified starch to give starch pastes having a solids content of up to 70% by weight. The starch in granular form, without the intermediate formation of a slurry, is continuously supplied to a reaction zone where it is subjected to the action of an enzyme (e.g., alpha amylase) in a stirred aqueous medium at an elevated temperature (50–98° C.) and pH of 4.5–8. Once the liquefaction is completed the liquefied starch is stabilized by deactivating the enzyme. A greater proportion of large molecules and a broader molecular weight distribution result as compared to a discontinuous process where the molecules are smaller and substantially the same size.

DE 37 31 293 A1 (laid open Apr. 8, 1980) discloses a process for continuously degrading and digesting starch. A dry starch powder together with liquid water or an aqueous starch suspension is charged to a stirred converter containing a starch degrading enzyme, preferably alpha amylase, while the temperature is increased to 70–90° C. by injecting steam at 120–125° C. and 2–4 bar. The product leaving the converter is treated with an enzyme deactivating agent before final dilution to the desired concentration. Starch pastes with a solids content of up to 80% and higher are obtained.

U.S. Pat. No. 4,921,795 (issued May 1, 1990 to F. A. Bozich, Jr.) discloses an improved slurry method for producing dextrin adhesives using alpha amylase in combination with glucoamylase. The function of the glucoamylase is to eliminate the limit dextrin problem and a mechanical shearing step. The alpha amylase randomly cleaves the α(1→4) linkages of the linear amylose molecules and cleaves the branched amylopectin molecules up to the (1→6) glucosidic linkages of the limit dextrin. The slurry is stirred sufficiently to create a vortex in the aqueous reaction slurry, thereby maintaining adequate mixing without shearing. The hydrolysis is allowed to continue until an optimal mix of fragment sizes is achieved (as indicated by a Brookfield viscosity of 1000–2000 cps at 20 rpm, 110° F., 45–55% solids, and 0 to 16% sodium borate pentahydrate). The enzyme is then inactivated. The Theological properties of the resultant slurry can be adjusted as needed.

EP 231,729 (published Aug. 4, 1993) discloses a two step process for the enzymatic degradation of flour. The first step involves treatment with alpha amylase. The second step involves treatment with beta amylase optionally in combination with pullulanase. The dry solids content of the suspension is as high as possible, e.g., 30–50%.

U.S. Pat. No. 5,445,950 (issued Aug. 29, 1995 to S. Kobayashi et al.) discloses a method for slightly decomposing a granular starch with an alpha amylase and/or glucoamylase at 10–65° C. to reduce the viscosity of the granular starch. The starch is decomposed 0.1–15%, preferably 0.1–1%.

There is a need for a process which can be used to prepare high solids, enzyme-converted starches.

SUMMARY OF THE INVENTION

The present invention is directed to a high solids enzyme conversion process for preparing a liquefied enzyme-converted starch, which comprises the steps of:

(a) adding, to a modified or unmodified, non-cold-water-soluble starch, water and a starch-hydrolyzing enzyme in an amount sufficient to produce a single phase powdered mixture without a visible free water phase;

(b) activating the enzyme by heating the powdered mixture to about the optimum temperature for the enzyme while maintaining a substantially constant moisture content (i.e., within ±5% from the starting moisture content) in the mixture;

(c) allowing the enzyme to hydrolyze the starch; and (d) optionally inactivating the enzyme.

The present invention is also directed to a high solids process for preparing enzyme-converted modified or unmodified granular starches which are prepared as above except that when an alpha amylase is used the total water content in step (b) is about 15–35% and when the enzyme is an enzyme other than alpha amylase or is an enzyme mixture containing alpha amylase the total water content is about 15–40%.

As used herein, "starch" is intended to include non-pregelatinized granular starches, pregelatinized granular starches, and starches which are pregelatinized but not cold-water-soluble.

As used herein, "single phase" means a mixture which has no visible free water, whereas a "slurry" consists of two phases, i.e., a water phase and a starch phase. The preferred total water content herein is about 15 to 40% by weight of the total mixture, except when a converted granular starch is being prepared with only alpha amylase where the total water content is about 15–35%.

The powdered or preferably liquid enzyme and sufficient water to give the desired total water content are dispersed onto a granular starch powder. The typical moisture content of granular starches is about 10–14%. Thus, sufficient water is added in step (a) to bring the total amount of water to the desired amount. As used herein, the term "total amount of water" refers to the total of the equilibrium moisture typically present in a granular starch and the added water.

If the moist single phase powdered mixture is subjected to a mixing process which kneads and compacts, such as that in typical dough mixing equipment or viscous polymer compounding equipment, it may, depending upon the water content and amount of solubles present, become a very high viscosity compact doughy mass before the onset of gelatinization and conversion. Continued mechanical shearing will raise the temperature and cause gelatinization and conversion.

When the powdered starch mixture contains a granular starch, as the powdered mixture is heated, the heat and moisture initiate the swelling of the starch granules and the starch is completely or partially gelatinized and simultaneously converted. When the powdered mixture contains a pregelatinized, non-cold-water-dispersible starch, the heat and moisture disperse the starch and the starch is fully gelatinized and simultaneously converted. As the starch is converted, usually the powder liquefies. Whether a liquefied product or a partially converted granular product results depends on the moisture content and temperature. For example, treating a waxy maize starch with alpha amylase at 35% moisture below 70° C. gives a partially hydrolyzed granular starch. However, at 40% moisture and above 95° C., a waxy maize starch is gelatinized, hydrolyzed, and liquefied by the alpha amylase. The peak viscosity of the native starch is never reached.

The dextrose equivalent (D.E.) is an indication of the degree of conversion as shown by the reducing sugar content of the maltodextrin.

The final product may be in the form of a syrup, a converted granular starch, or a mixture of the syrup and the converted granular starch. As used herein, "syrup" covers liquids and viscous pastes. The resulting starch syrup is obtained at a high solids content (e.g., at least 60%, typically 65–75% by weight). The syrup may be spray dried, belt-dried, or freeze dried. The enzyme-converted starch may be recovered from the starch syrup as a water-soluble powder. If desired, the sugar by-products may be removed from the granular converted starch by washing.

Microporous granular converted starches can also be prepared by the high solids, enzyme conversion process using a glucoamylase alone or mixed with an alpha amylase.

Optionally, an enzyme activator such as certain inorganic salts and/or a pH adjuster such as an acid, a base, or a buffer may be used.

The enzyme may be activated by direct or indirect heating and/or pH adjustment to the optimum temperature and pH for the particular enzyme used. The enzyme may be inactivated by reducing the pH, adding an inhibiting salt, or increasing the temperature.

The water content during the conversion is affected by the product solids, the condensation of injected steam used for direct heating, and evaporation during the conversion. The product solids are increased by the hydrolysis. During conversion to a D.E. of 100, the dry weight of the starch is increased by 11.11% due to water covalently bound to the hydrolysis reaction products. This dry weight increase is proportional to the degree of conversion. The solids are decreased due to the condensed steam and increased by evaporation.

The powdered mixture of the starch, water, and enzyme does not require stirring during the enzyme conversion step.

In contrast to prior art enzyme conversion processes, the process is carried out at such a high solids content that the mixture is a single phase without visible free water.

DESCRIPTION OF THE PREFERRED EMBODIMENTS

Starches for use in the high solids, single phase enzyme conversion process and in the preparation of the enzyme converted starches can be derived from any source. Typical sources for the starches are cereals, tubers, roots, legumes, fruits and hybrid starches. Suitable native sources include corn, pea, potato, sweet potato, sorghum, wheat, rice, waxy maize, waxy tapioca, waxy rice, waxy barley, waxy wheat, waxy potato, waxy sorghum, starches containing greater than 40% amylose (also referred to as high amylose starches), and the like.

It may be possible to convert flours provided effective enzyme levels are used to obtain sufficient conversion.

Granular starches which have not been pregelatinized are preferred. Granular pregelatinized starches are also useful herein. The pregelatinized granular starches are prepared by processes known in the art. The pregelatinization is carried out in such a way that a majority of the starch granules are swollen, but remain intact. Exemplary processes for preparing pregelatinized granular starches are disclosed in U.S. Pat. Nos. 4,280,851, 4,465,702, 5,037,929, and 5,149,799, the disclosures of which are incorporated herein by reference. Predispersed (i.e., pregelatinized starches) can also be used in the high solids, single phase enzyme conversion process provided they are not cold-water-soluble. They can be prepared by jet-cooking and spray-drying.

As will be shown hereafter, the various granular starch bases have different enzyme susceptibilities in this high solids process. Granular high amylose starches are more difficult to convert in the high solids, single phase process. Chemically derivatizing the starch can lower the gelatinization temperature and makes it easier to carry out the conversion.

The starch may be chemically or physically modified. Chemical modifications include heat- and/or acid-conversion, oxidation, phosphorylation, etherification, esterification, chemical crosslinking, conventional enzyme modification, and the like. These modifications are preferably performed before the starch is enzyme converted. Procedures for modifying starches are described in the chapter "Starch and Its Modification" by M. W. Rutenberg, pages 22–26 to 22–47, Handbook of Water Soluble Gums and Resins, R. L. Davidson, Editor (McGraw-Hill, Inc., New York, N.Y. 1980).

Physically modified starches, such as the thermally-inhibited starches described in WO 95/04082 (published Feb. 9, 1995), are also suitable for use herein.

Suitable enzymes for use herein include bacterial, fungal, plant, and animal enzymes such as endo-alpha-amylases which cleave the 1→4 glucosidic linkages of starch, beta amylases which remove maltose units in a stepwise fashion from the non-reducing ends of the alpha-1,4-linkages, glucoamylases which remove glucose units in a stepwise manner from the non-reducing end of the starch molecules and cleave both 1→4 and 1→6 linkages, and debranching enzymes such as isoamylase and pullulanese which cleave the 1→6 glucosidic linkages of amylopectin-containing starches. Alpha amylases or mixtures thereof with other enzymes are preferred and are used for preparing the enzyme-converted starches having unique bimodal or polymodal molecular weight profiles.

Significant conversion (45%) results when a non-pregelatinized, granular, amylopectin-containing starch is treated with a debranching enzyme such as pullulanese. The resulting debranched starches have a much higher peak molecular weight than enzyme converted starches produced by conventional debranching of a cooked dispersed starch. In addition, the molecular weight of an enzyme debranched waxy maize is different from that of an alpha amylase converted waxy maize even under the same conversion conditions.

Enzymes can be purified by selective absorption or precipitation, but many commercial products contain significant amounts of impurities in the form of other enzymes, as well as in the form of inert protein. For example, commercial bacterial "amylases" will sometimes also contain "proteinases" (enzymes which break down protein). After extraction and partial purification, commercial enzymes are sold either as powders or as liquid concentrates.

Process conditions for the use of a particular enzyme will vary and will usually be suggested by the supplier. The variables include temperature, pH, substrate solids concentration, enzyme dose, reaction time, and the presence of activators. Very often there are no absolute optimum reaction conditions. The "optimum" pH may depend on temperature; the "optimum" temperature may depend on reaction time; the "optimum" reaction time may depend on cost, and so on. The reaction time can vary from 10 minutes to 24 hours or more, typically 1 to 14 hours for alpha amylase. The recommended conditions therefore are usually compromises.

The stability of an enzyme to adverse conditions is usually improved by the presence of its substrate. Some enzymes are also stabilized by certain salts (bacterial amylase is stabilized by calcium salts). It is necessary rigorously to exclude heavy metals and other enzyme poisons, such as oxidizing agents, from an enzyme reaction. These materials usually result in permanent inactivation (i.e., denaturization) of the enzyme. There are many instances, however, where enzyme activity is reduced reversibly, frequently by the products of the reaction (product inhibition) or by a substance which is structurally related to the usual substrate (competitive inhibition). Reversible inhibitors complex temporarily with the enzyme and therefore reduce the amount of enzyme available for the normal reaction.

Typical enzyme reaction conditions are discussed in "Technology of Corn Wet Milling" by P. H. Blanchard, Industrial Chemistry Library, Vol. 4 (Elsevier, New York, N.Y. 1992).

TEST PROCEDURES

Dextrose Equivalent

A Fehling Volumetric Method, as adapted from the Eynon-Lane Volumetric Method #423 in the Cane Sugar Handbook by Spencer and Mead (John Wiley and Son Inc.), is used to determine the D.E.

A starch solution (w/v) of known concentration on an anhydrous starch basis is prepared. The usual concentration is 10 g/200 ml. The starch solution is transferred to a 50 ml burette. To 50 ml of distilled water in a 500 ml Erlenmeyer flask are added 5 ml each of Fehling Solutions A and B by pipette. Fehling Solution A contains 34.6 g of copper sulfate ($CuSO_4.5H_2O$) dissolved in and brought to volume in a 500 ml volumetric flask. Fehling Solution B contains 173 g of Rochelle salt ($NaKC_4H_4O_6.4H_2O$) and 50 g of sodium hydroxide (NaOH) dissolved in and brought to volume in a 500 ml volumetric flask. The Fehling Solutions are standardized against Standardized Dextrose obtained from the Bureau of Standards.

To determine the Fehling Factor, the test procedure is followed except that 0.5000 anhydrous grams of dextrose per 200 ml of distilled water is used as the test solution. Using the following formula the factor is then computed:

Factor=100×ml used in titration×q dextrose/ml/100

The factor applies to both Fehling solutions A and B and is computed to 4 decimal places. The contents of the flask are brought to a boil over a hot plate. The starch solution, while at a boil, is titrated to the distinctive reddish-brown colored end point (precipitated cuprous oxide complex). The ml of starch solution used is recorded.

The Dextrose Equivalent (DE) is calculated using the formula:

% DE=(Fehling Factor)×100/(g/ml starch concentration×ml starch solution)

where "starch solution" equals the ml of starch solution used in the titration to reach the end point and "starch concentration" equals the concentration of the starch solution on an anhydrous basis expressed in g/ml.

Gel Permeation Chromatography (GPC)

Molecular weight (MW) distribution is determined using a Water Associates GPC-150C model with a refractive index (RI) detector. Two PL gel columns ($10^5$ and $10^3$) made of highly crosslinked spherical polystyrene/divinylbenzene, obtained from Polymer Laboratories (Amherst, Mass.), are connected in sequence. Dextrans from American Polymer Standards Corp. (Mentor, Ohio) are used as the standards. The experimental conditions are a column temperature of 80° C., a flow rate of 1 ml/min. The mobile phase is dimethyl sulfoxide (DMS) with 5 mM of sodium nitrate ($NaNO_3$). The sample concentration is 0.1% and the injection volume is 150 µl.

Brookfield Viscometer Procedure

Test samples are measured using a Model RVT Brookfield Viscometer and the appropriate spindle (the spindle is selected based on the anticipated viscosity of the material). The test sample is placed in position and the spindle is lowered into the sample to the appropriate height. The viscometer is turned on and the spindle is rotated at a constant speed (e.g., 10 or 20 rpm) for at least 3 revolutions before a reading is taken. Using the appropriate conversion factors, the viscosity (in centipoises) of the sample is recorded.

EXAMPLES

In the examples which follow, non-pregelatinized granular starches are used unless it is otherwise stated and the various enzymes described hereafter were used.

The alpha amylases were BAN 120L and TERMAMYL. They were obtained from Novo Nordisk. BAN is a conventional alpha amylase with an optimum temperature of approximately 70° C., optimum pH of 6.0–6.5, an activity of 120 KNU/g, and recommended usage (based on the weight of the starch) of 0.005–1.0%, preferably 0.01–0.5%. TERMAMYL is a heat-stable alpha amylase with an optimum temperature greater than 90° C., an activity of 120 KNU/g, and recommended usage (based on the weight of the starch) of 0.005–1.0%, preferably 0.01–0.5%. One Kilo Novo unit (1 KNU) is the amount of enzyme which breaks down 5.26 g of starch (Merck, Amylum Solubile, Erg. B6, Batch 994 7275) per hour in Novo Nordisk's standard, method for determining alpha amylase using soluble starch as the substrate, 0.0043 M calcium content in solvent, 7–20 minutes at 37° C. and pH 5.6.

The mixture of alpha amylase and glucoamylase used was ASPK 27 obtained from Daikin Kogyo, Kabushigi, Kaisha, Osaka, Shi Kibanoku, Ichome 12-39 Japan. The optimum conditions are not disclosed.

The barley beta amylase used was SPEZYME BBA 1500 which was obtained from Finnsugar Group. The optimum conditions for this enzyme are pH 5.0–7.0 and a temperature of 55–65° C. It has an activity of 1500 Dp°/ml and its recommended usage (based on the weight of the starch) is 0.1–2.0%, preferably 0.2–0.8%. One Degree of Diastatic Power (Dp°) is the amount of enzyme contained in 0.1 ml of a 5% solution of the sample enzyme preparation that produces sufficient reducing sugars to reduce 5 ml of Fehling Solution when the sample is incubated with 100 ml of substrate for 1 hour at 20° C.

Amyloglucosidase (AMG 300L) is an exo-1,4-alpha-D-glucosidase. Optimum conditions are pH 4.5 and 60° C. It has an activity of 300 AGU/ml recommended usage (based on the weight of the starch) of 0.005–1.0%, preferably 0.01–0.5%. One Novo Anhydroglucosidase Unit (AGU) is defined as the amount of enzyme which hydrolyzes 1 micro-mol of maltose per minute using maltose as the substrate at 25° C., pH 4.3 for 30 minutes.

The debranching enzyme used is PROMOZYME 600L (pullulanase) which was also obtained from Novo Nordisk. It is a heat-stable debranching enzyme with an optimum temperature of 60° C. and optimum pH of 5.1. It has an activity of 200 PUN/g and the recommended usage (based on the weight of the starch) is 1–15%, preferably 2–10% PUN/g. It is a concentrated form of PROMOZYME with an activity of 600 PUN/ml concentrate. One Pullulanese Unit Novo (PUN) is the amount of enzyme which hydrolyzes pullulan, liberating reducing carbohydrate with a reducing power equivalent to 1 micro-mol glucose per minute under the conditions discussed hereafter. The optimum conditions for this enzyme are pH 5.0 (0.05 M citrate buffer) and a temperature of 40° C.

Example 1

This example shows the effect of the water content on the degree of hydrolysis of a granular starch.

Waxy maize (1,000 g) was placed in a Ross Mixer with standard blades (Charles Ross & Son Co., Hauppauge, N.Y.). A mixture of 0.1% each of TERMAMYL and BAN was used. Sufficient water was added to give a total water content of 20% and 40%.

Comparative experiments were done on native waxy maize, i.e., with the equilibrium moisture content of 11%. In one experiment, the enzymes (0.2% of each of BAN 120L and TERMAMYL) were added to the starch as fine drops from a disposable micropipette. The starch and enzymes were further mixed in a Hobart mixer for 10 minutes. Portions (100 g each) of the mixture were transferred to two 16 ounce jars and placed in a oven set at 98° C. for 24 hours. In the other experiment, 1,000 g of the starch (10.3% moisture) was placed in a Hobart mixer bowl. TERMAMYL (0.2% based on starch) was mixed with 495 ml. of tap water (pH 6.2) and added to the starch to give a total moisture content of 40%. Mixing of the starch, enzyme, and water was carried out for ten minutes at low speed. The mixture was air-dried at room temperature to 11.4% moisture. The air-dried starch (100 g) was placed in a 200 ml. jar and sealed. The jar was then put in an oven at 98° C. for 24 hours. The resulting products had little, if any, conversion compared to the base waxy maize starch when examined by GPC.

Figure 1:
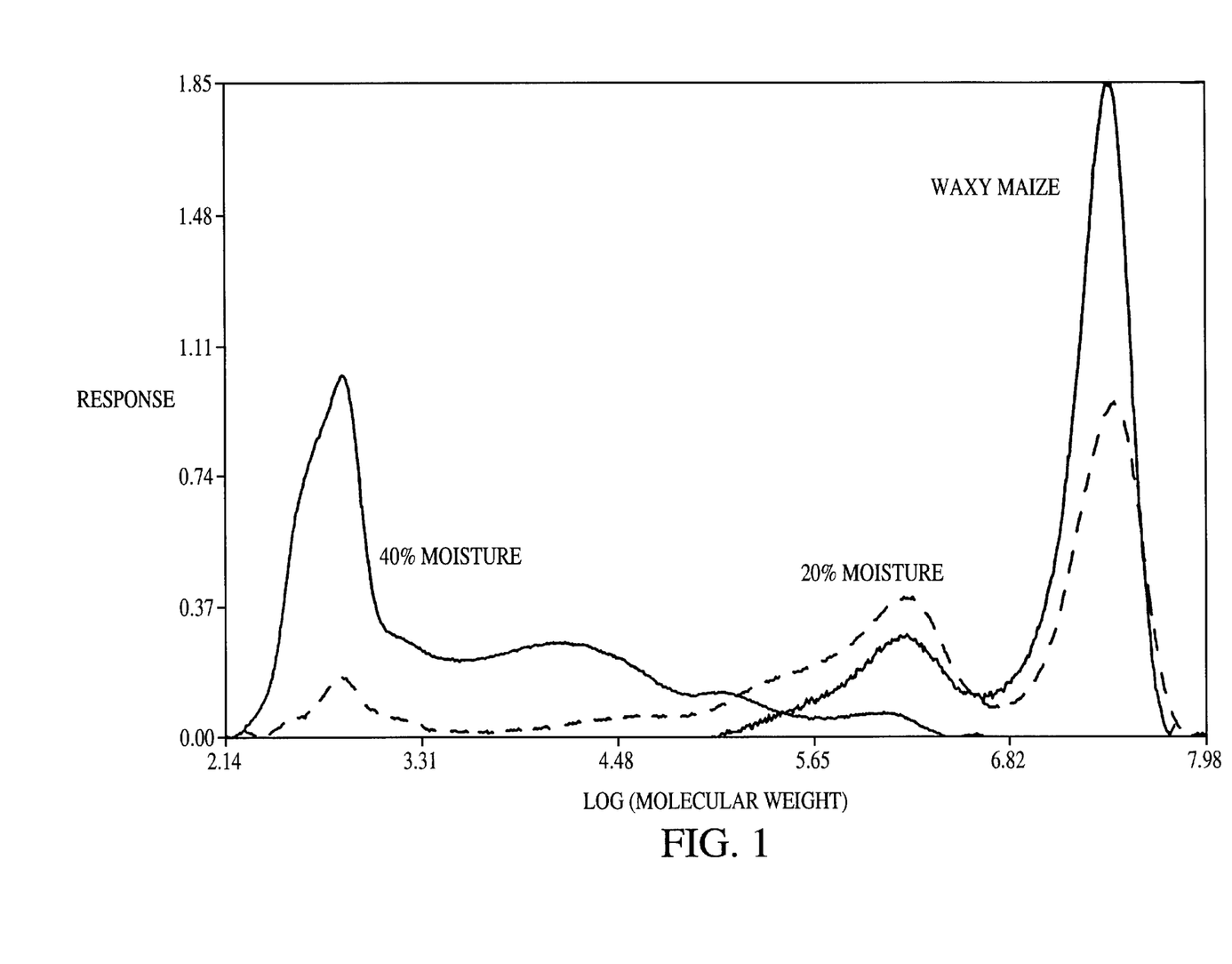
FIG. 1 shows the molecular weight distributions of a non-converted native waxy maize starch (11% total moisture) and enzyme-converted waxy maize starches which were hydrolyzed at 20% and 40% total moisture using a mixture of alpha amylases.

FIG. 1 shows the molecular weight distribution of the non-hydrolyzed native waxy maize and the waxy maizes hydrolyzed at 20 and 40%. Under the same conditions, the amount of total water had a great effect on the degree of conversion as shown by the molecular weight of the final products. Increasing the water content, generally increases the degree of conversion. At the equilibrium moisture content (no additional water), there was virtually no enzyme conversion of the starch.

Example 2

This example describes a series of enzyme conversions run in a ten gallon gate mixer reactor using BAN (B), TERMAMYL (T), SPEZYME (S) and mixtures thereof. In some cases, the enzyme was added in two steps.

The internal dimensions of the tank were 16 inches tall by 16 inches in diameter. The gate agitator, made from ½ inch wide by 2 inch deep stainless steel bar stock, had four vertical rakes 10½ inches tall. The outside rakes cleared the inside tank wall by ½ inch; the inside rakes were 3¼ inches from the outside set. Attached to the tank top were four breaker bars, of the same bar stock, located 1¾ and 5¼ inches in from the tank wall. An electric drive, variable from 0 to 60 rpm, powered the agitator. A vent in the tank top provided variable draft forced exhaust. The tank sides and bottom were jacketed for steam heating or water cooling. A ½ inch diameter steam injection port was provided in the side wall 1 inch above the tank bottom. A thermocouple probe was attached to the bottom of one outside breaker bar. In the tank bottom a 2 inch port with a ball valve was provided for product draw off. For these conversions a removable metal plug was inserted into the draw port, flush with the tank bottom, to eliminate the possibility of a portion of the initial dry charge receiving non-uniform moisture, enzyme, or heat.

For each conversion 33 pounds of a commercially dry granular starch was added to the tank. The enzyme charge was diluted with sufficient water to bring the charge to 25 percent moisture on an anhydrous basis. This water/enzyme mix was added to the starch with mixing. The mixture, after addition of the enzyme/water mix, was a blend of dry starch and moist starch aggregates less the one half inch in diameter.

At this point, the agitator is turned off for about 30 minutes to allow the water to diffuse throughout the starch. The starch, after this rest, was a moist flowable powder.

The mixture was heated, generally by injection of live steam (at 32 psi except where indicated otherwise) into the mixture and/or optionally by heating the tank jacket. Typically, the mass was mixed during heating, but this was not required. Mixing only improved heat transfer.

As the granular starch gelatinized (or the cold-water-insoluble predispersed starch was solubilized), it was converted and the reaction mixture changed from a moist powder to a wet doughy mass and then to a dispersed syrup. These changes occurred as the temperature was increased from 50° C. to 90° C. The temperature at which the onset of liquefaction occurred varied depending on the water activity, enzyme activation temperature, and starch type.

In this vented tank, there was some loss of moisture during the full heating cycle. When the injection steam was shut off, the temperature was maintained at the indicated temperature with jacket heating for 30 minutes. The batch was then cooled to less than 50° C. and drawn off. Optionally, the pH was reduced to 3.5 with phosphoric acid and the mixture was held for 30 minutes to deactivate any residual enzyme. The pH was readjusted if required.

The starch base used, enzyme and amount, and holding temperature are shown in the table below. The solids content and dextrose equivalent (D.E.) are also shown. For the chemically derivatized starches the degree of substitution (D.S.) is given. The reagents used to derivatize the starches were propylene oxide (PO), ocentylsuccinic anhydride (OSA), and acetic anhydride ($Ac_2O$), and 3-chloro-2-hydroxypropyl trimethylammonium chloride (Quat.) which were used in amounts sufficient to provide the indicated D. S. When the starch base was a fluidity starch (an acid converted starch), the water fluidity (W. F.) is shown. One of the starch bases was a predispersed starch which was jet-cooked (JC) and spray-dried (SD).

| Sample No. | Starch Base | Enzyme | Hold Temp. | Converted Starch [Dextrin] | | |
|---|---|---|---|---|---|---|
| | | | | Solids (%) | DE | D.S. |
| 1' | Waxy Maize 35 WF, PO | 0.045 B 0.045 T | 90–95° C. | 62.2 | 13.7 | 0.16 |
| 2 | Waxy Maize 35 WF, PO | 0.09 T | 90–95° C. | 70.9 | 11.0 | 0.16 |
| 3 | Waxy Maize 35 WF, PO | 0.18 T | 90–95° C. | 62.8 | 10.6 | 0.16 |
| 4 | Waxy Maize PO | 0.09 T | 90–95° C. | 68.9 | 13.2 | 0.09 |
| 5 | Waxy Maize PO, JC/SD | 0.09 T | 90–95° C. | 68.5 | 4.1 | 0.09 |
| 6 | Waxy Maize OSA | 0.09 T | 90–95° C. | 60.2 | 15.2 | 0.02 |

-continued

| Sample No. | Starch Base | Enzyme | Hold Temp. | Converted Starch [Dextrin] Solids (%) | DE | D.S. |
|---|---|---|---|---|---|---|
| 7 | Waxy Maize 35 WF, PO | 0.045 T 0.045 T | 90–95° C. | 60.0 | 7.4 | 0.16 |
| 8 | Waxy Maize | 0.09 T | 90–95° C. | 65.0 | 18.7 | — |
| 9 | Waxy Maize Quat. | 0.09 T | 90–95° C. | 71.0 | 22.2 | 0.04 |
| 10 | Tapioca | 0.09 T | 90–95° C. | 56.7 | 6.9 | — |
| 11 | Waxy Maize | 0.045 B 0.045 T | 90–95° C. | paste | 13.6 | — |
| 12 | Waxy Maize | 0.0045 B 0.222 S | 60–64° | 55.0 | 3.2 | — |
| 13** | Waxy Maize Ac$_2$O | 0.09 T 0.09 T | 90–95° C. | ~60 | — | 1.3 |
| 14 | Waxy Maize 35 WF, PO | 0.09 T | 90–95° C. | 69.0 | — | 0.16 |
| 15*** | 1:1 Mixture of 35 WF, PO Waxy Maize crosslinked with Adipic/ Acetic Anhydride (D.S. ~0.02) and 80 WF, PO Tapioca (D.S. 0.08) | 0.09 T 0.09 T | 90–95° C. | 65 | — | — |

*For Sample No. 1, the steam pressure was 8 psi.
**For Sample Nos. 7, 13, and 15, the enzyme addition was carried out in two steps. Sample No. 13 was prepared using the procedure described in U.S. Pat. No. 5,321,132 (issued June 14, 1994 to R. L. Billmers et al.), the disclosure of which is incorporated herein by reference.

The results show that various starches can be converted using the high solids, single phase enzyme conversion process, including unmodified starches, chemically derivatized starches, fluidity chemically derivatized starches, and chemically derivatized and crosslinked starches. Even a highly derivatized starch such as Sample No. 13 was converted.

Example 3

This example shows the conversion of a granular waxy maize starch by glucoamylase.

A total of 1,000 g of a waxy maize starch (10.5% moisture) was placed in a double planetary Ross Mixer with standard blades. Water (490 ml) was adjusted to pH 4.5 by mixing with a 1:3 hydrochloric acid:water (w/w) and 1% glucoamylase AMG 300L was added. The enzyme solution was then added to the mixer in an amount sufficient to give 40% total water. The mixer was closed, and the starch and the enzyme solution were mixed for 5 minutes at room temperature with the mixer setting at two. The resulting mixture was a moist powder with no visible free water. The temperature of the mixture was then increased to 60° C. to activate the glucoamylase. After the mixture was held at 60° C. for 2 hours, a sample (265 g) was removed from the mixer.

To determine the amount of starch solubilized after enzyme treatment, 5 g of the sample was slurried in 10.03 ml of water and centrifuged at 10,000 rpm for 10 minutes. The solubles were 3.8% in the supernatant as measured by a refractometer. Through calculation, and after correcting for the solubles in the enzyme solution, the amount of starch solubilized during the enzyme conversion was determined to be 12.6%, based on the dry weight of starch.

The remaining 260 g of the sample was slurried in 400 ml of water, adjusted to pH 3.4 with a 3:1 water: hydrochloric acid solution, held at pH 3.4 for 1 hour, readjusted to pH 5.5, filtered, and air-dried to provide Sample A.

The remaining mixture was held at 60° C. for another 3 hours (5 hours total). A sample (~75 g) was removed. The solubilized material was determined to be 19.7%, based on dry weight of starch. The remaining sample was pH adjusted, filtered, and air-dried to provide Sample B.

The remaining mixture was heated to 75° C. and held at 76–77° C. for 1 hour. The product was somewhat doughy due to the swelling of the starch granules as well as the solubles (i.e., glucose) produced by the glucoamylase conversion. The product was broken up and air-dried to provide Sample C.

The treatment conditions and % solubles are summarized below.

| Sample | Treatment/Conditions | % Solubilized |
|---|---|---|
| A | 60° C., 2 hours, washed | 12.6 |
| B | 60° C., 5 hours, washed | 19.7 |
| C | 60° C., 5 hours, 75° C., unwashed | 32* |

*Low MW material (glucose) integrated from the GPC curve.

Figure 2:
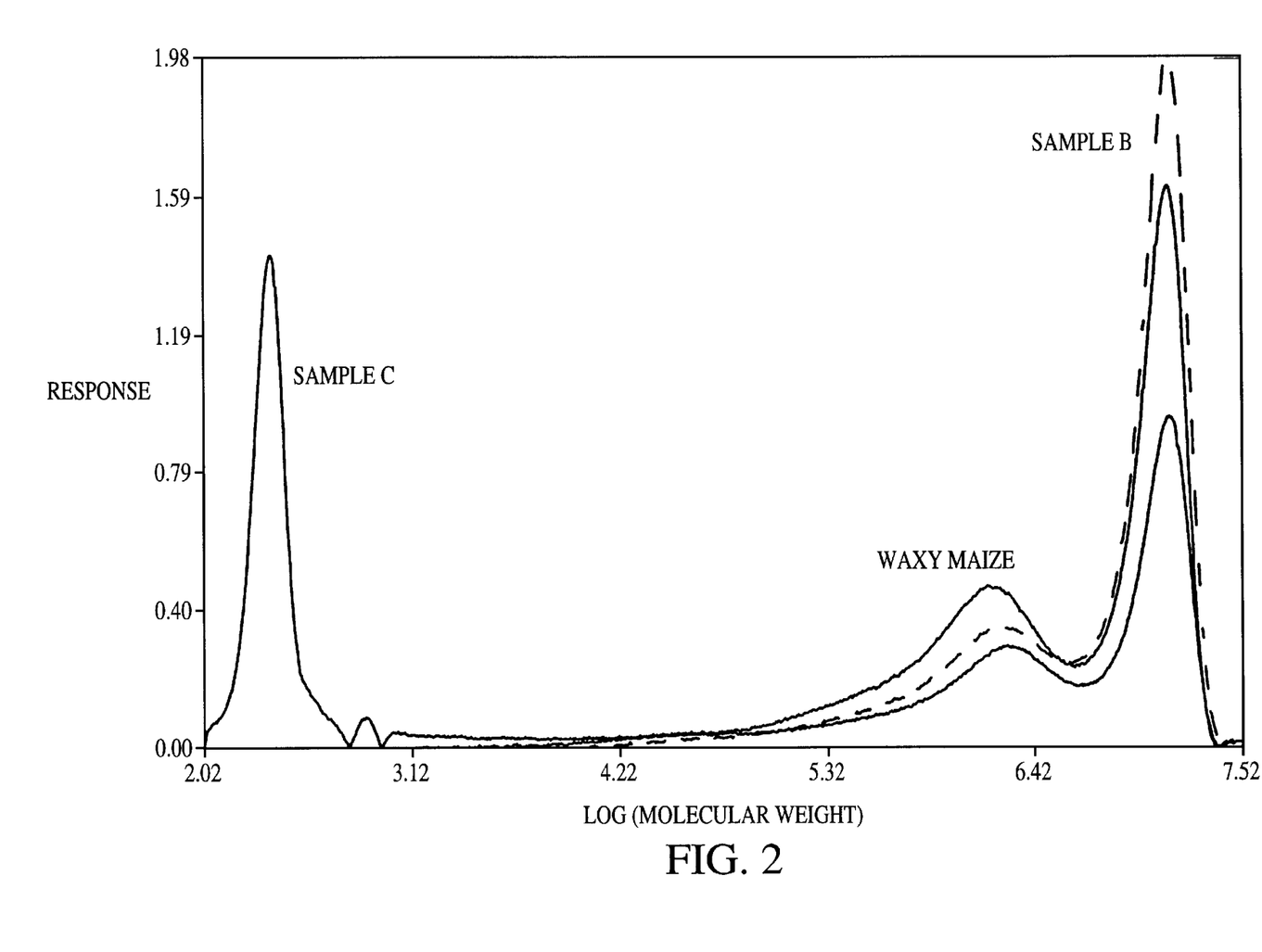
FIG. 2 shows the molecular weight distributions of a non-converted waxy maize starch (Sample A) and a glucoamylase-converted waxy maize starch which was washed with water (Sample B) and of a glucoamylase-converted waxy maize starch which was not washed with water (Sample C). Sample C shows a glucose peak.

FIG. 2 shows the molecular weight distribution of a non-converted waxy maize and glucoamylase-converted waxy maize starches. For the glucoamylase-converted waxy maize, if the product was not washed with water (Sample C), the product showed a glucose peak. When the glucoamylase-converted waxy maize was washed with water (Sample B), the glucose peak is not present. Both Samples B and C show large molecular weight peaks similar to the native waxy maize with virtually no intermediate molecular weight materials. The fact that the glucoamylase-converted waxy maize contains no intermediate MW material and the washed product has a similar MW distribution indicates that the glucoamylase selectively hydrolyzed some starch molecules in the granules and left the rest of the molecules intact.

Selective and localized attack by the glucoamylase on the starch molecules in the granules is also shown in Scanning Election Micrographs (SEM) of the enzyme-converted starches.

Sample C, the unwashed sample, was comprised of particle clusters which were irregular and ranged from under 50 microns to approximately 300 microns. The particle clusters formation was probably due to the glucose which glued the granules together. The surfaces in the detailed views show pitting with some granules highly pitted and some relatively undisturbed. The typical pit was sub-micron in diameter.

Little, if any, particle clusters were observed in Sample A, indicating that after the glucose was washed away, the material was well-dispersed into single, individual granules. Again, pitting occurred in some granules while others were relatively unpitted.

Example 4

This example shows the conversion of a granular waxy maize using a mixture of alpha amylase and glucoamylase.

Using the procedure described previously, waxy maize was treated with 1% ASPK 27 at 50° C., 40% total water. A dry powdered starch was recovered after the 5.5 hour conversion. A significant production of glucose was shown in the GPC curve of the unwashed enzyme-converted product. SEM also revealed pin holes in the enzyme-converted granules as described previously.

Example 5

This example shows the preparation of a novel maltodextrin having a unique molecular weight profile by converting a waxy maize starch with the debranching enzyme PROMOZYME.

The starch was treated with PROMOZYME as previously described using 1,000 g of waxy maize starch and 40% total water except that the pH of the water was adjusted to 5.10 and 0.3% of the debranching enzyme was used. The starch and enzyme mixture was held at 58–60° C. for 24 hours. The final product was somewhat doughy and the starch granules appeared to be agglomerated.

Figure 3:
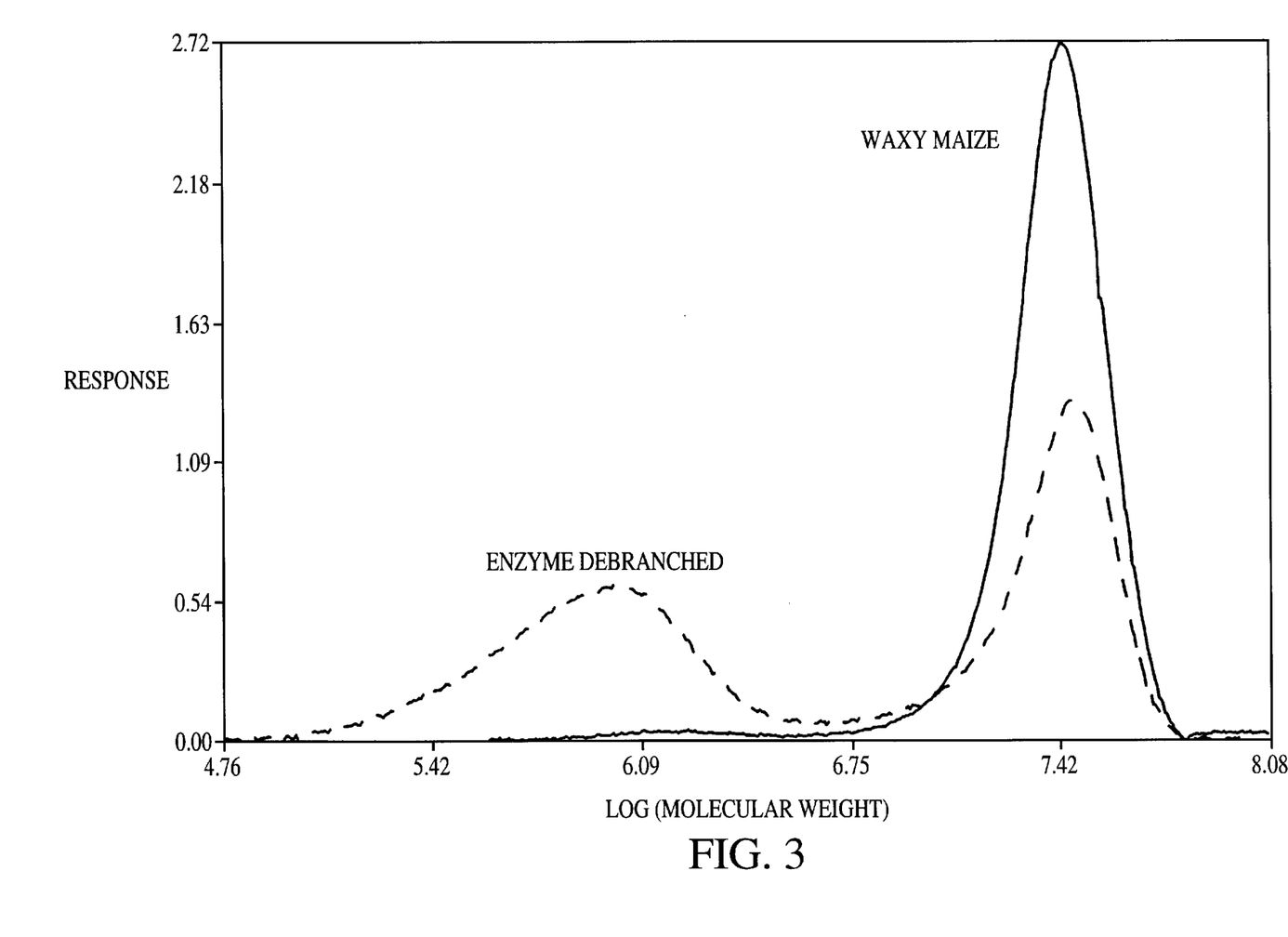
FIG. 3 shows the molecular weight distributions of a non-debranched waxy maize starch and an enzyme-debranched waxy maize starch.

FIG. 3 shows the molecular weight distribution of the waxy maize base and the enzyme-debranched waxy maize as determined by GPC. From the integration of the areas, about 45% of the waxy maize was converted compared to the base. The conversion was not due to glucoamylase or beta amylase because no glucose or maltose by-products were produced.

Figure 4:
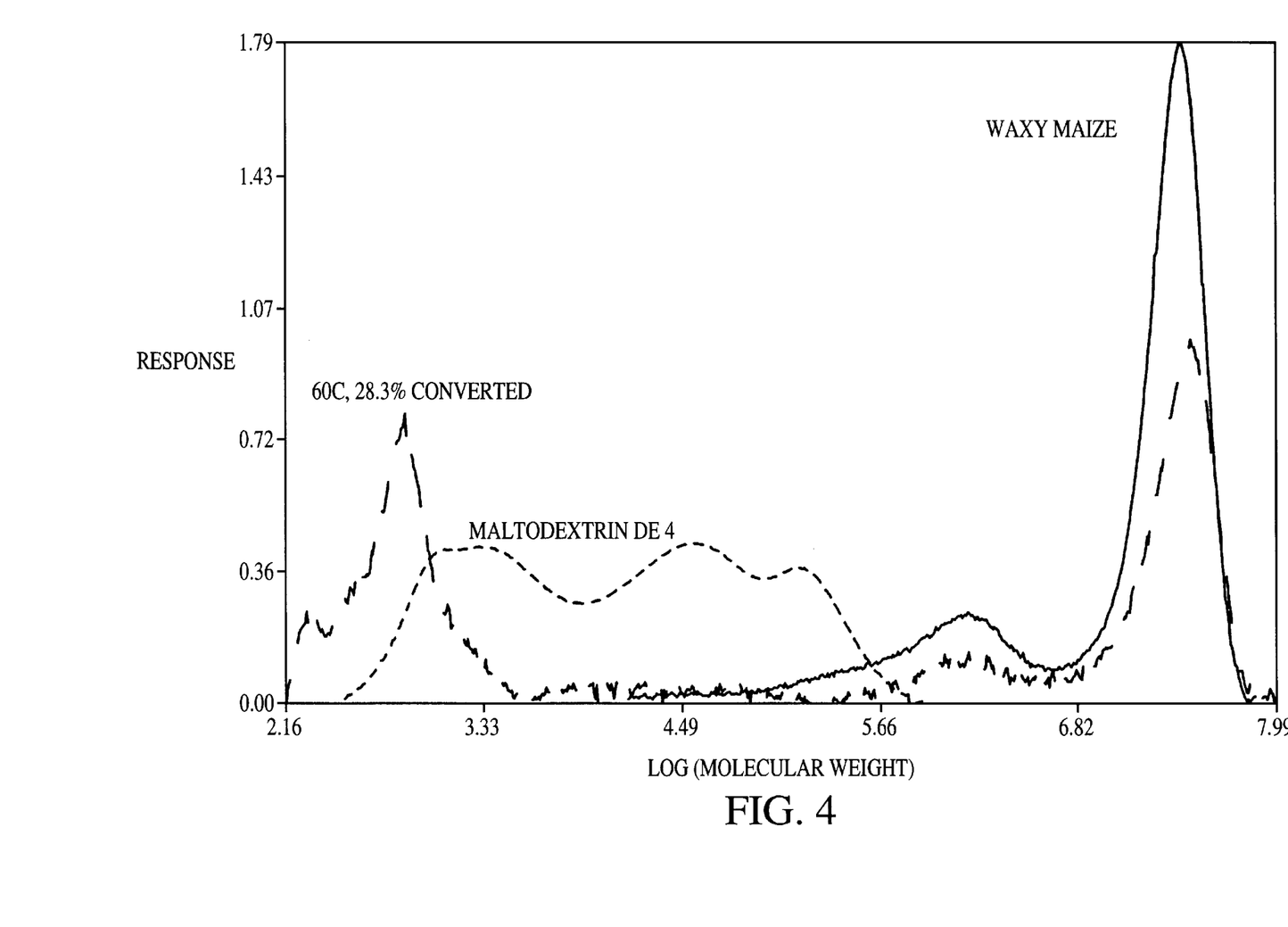
FIG. 4 shows the molecular weight distributions of alpha amylase-converted maltodextrins (28.3% and 60.2% converted) which are a unique mixture of low molecular weight oligosaccharides and high molecular weight saccharides with virtually no intermediate molecular weight maltodextrins. A commercial waxy maltodextrin (DE 4) is also shown for comparison.

The molecular weight distributions of the PROMOZYME-debranched waxy maize and an alpha-amylase-converted waxy maize (Ban) were compared (see FIG. 4). Both enzyme treatments were done at 60° C. and 40% water. The PROMOZYME-converted waxy maize and BAN-converted waxy maize had very different MW distributions. The alpha-amylase-converted waxy maize had a mixture of low molecular weight oligosaccharides and large molecular weight molecules, with peak molecular weights at 1,000 and $3.2 \times 10^7$, respectively and with a very low level of intermediate molecular weight materials. In contrast, the PROMOZYME-debranched waxy maize had a significant amount of materials with peak molecular weights at $10^6$.

If you completely disperse granular waxy maize starches and then debranch them with PROMOZYME, the resulting debranched materials will have a much lower molecular weight and different profiles than for the above debranched material.

Example 6

This example shows the preparation of another novel maltodextrin with a unique molecular weight profile prepared by the single phase high solids process.

Waxy maize (1,000 g) was placed in the Ross Mixer. Tap water (485 ml at pH 6.5) was mixed with 0.2% of BAN 120 L and the mixture was added to the Ross Mixer. The total water was 40%. The mixer was closed, and the starch and the enzyme solution were mixed for 10 minutes at room temperature with the mixer setting at 1. The temperature was then increased to 60° C., and the mixture was held at that temperature for 2 hours with the mixer setting at 3. A sample (about 100 g) was taken out and air-dried for GPC analysis. The temperature was then increased to 95° C. to inactivate the enzyme and the mixture was held at 95° C. for 15 minutes. The starch remained powdery even after being hydrolyzed at 60° C. for 2 hours. When the temperature was raised to 95° C., the starch was liquified. A sample (about 100 g) was taken our and air-dried on a glass plate for GPC analysis.

The resulting maltodextrin shows unusual molecular weight distributions when compared to a commercial waxy maize maltodextrin (DE 4) and to native waxy maize (see FIG. 4). At 60° C., 28.3% of the waxy maize was converted, whereas at 95° C., 60.2% of the waxy maize was converted. The maltodextrin prepared by the single phase process is a mixture of low molecular weight oligosaccharides and high molecular saccharides, with peak molecular weights of 1,000 and $3.2 \times 10^7$, respectively, and with virtually no intermediate molecular weight maltodextrins.

Example 7

This example shows the conversion of a chemically derivatized high amylose starch (Hylon VII-70% amylose).

A hydroxypropylated Hylon VII (D.S. 0.47) was hydrolyzed by alpha amylase using the procedure of Example 1, using 1,000 g of starch, 40% total water, and 0.2% TERMAMYL. The starch was liquefied after 4 hours at 98° C. and upon cooling the final product was a viscous solution.

Figure 5:
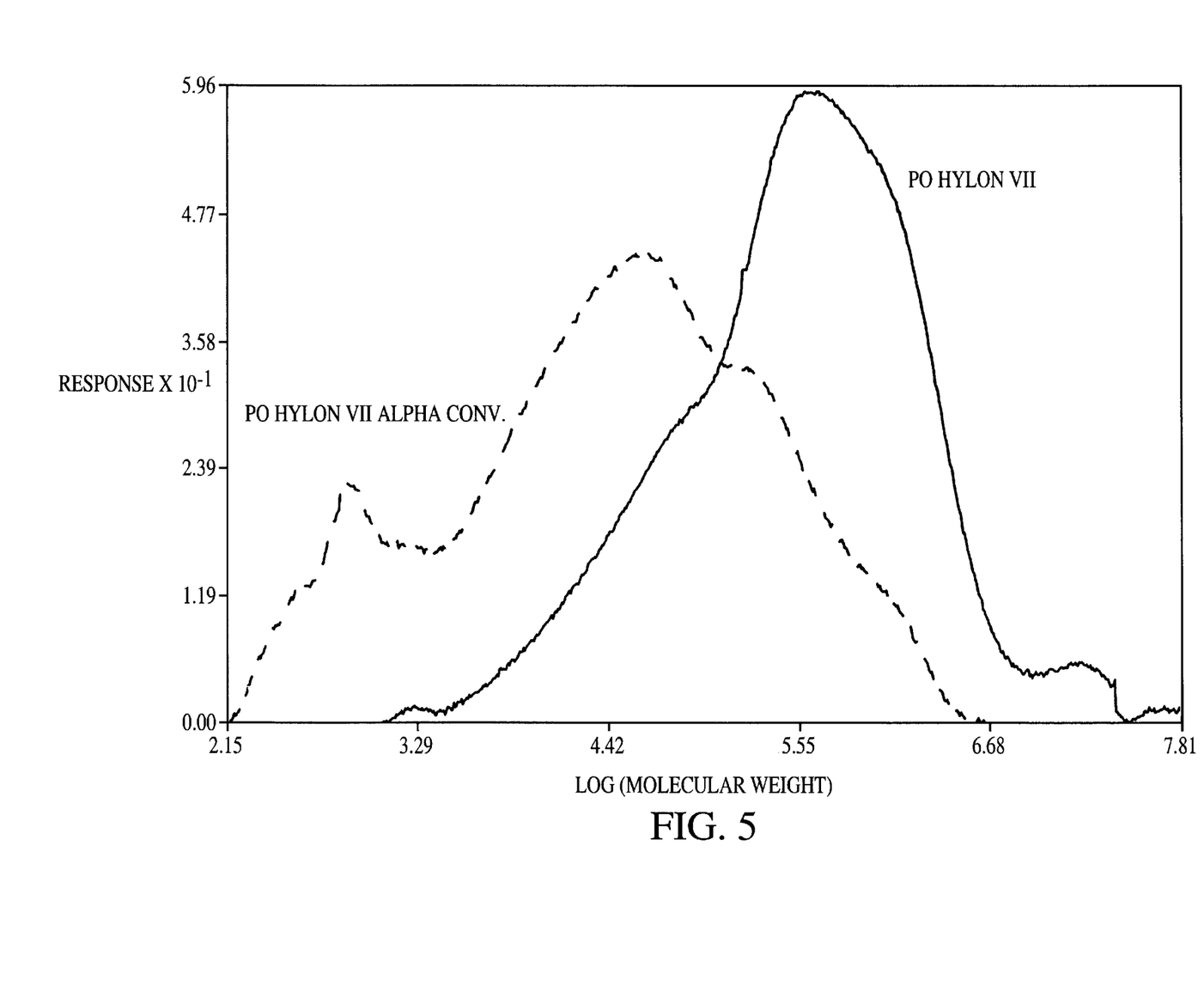
FIG. 5 shows the molecular weight distributions of a non-converted, hydroxypropylated high amylose starch (PO Hylon VII) and an alpha amylase-converted hydroxypropylated high amylose starch (PO Hylon VII).

FIG. 5 shows the molecular weight distribution of the hydroxypropylated Hylon VII and the alpha amylase converted hydroxypropylated Hylon VII.

Example 8

This example shows the conversion of a waxy maize starch ester using the single phase, high solids process.

An OSA-treated waxy maize was treated with a mixture of alpha amylase and beta amylase as described in Example 1, using 1,000 g of starch, 40% total water, and a mixture of 1 g of BAN 120 L and 0.5 g of SPEZYME. The mixture was held at 60° C. for 4 hours. A doughy material was formed. The product was broken up and air-dried. Part of the product (400 g) was slurried in 1,000 ml of water, adjusted to pH 3.0 for 30 minutes with 0.1 M hydrochloric acid, adjusted back to pH 6.0 with 3% sodium hydroxide, and spray-dried.

The results show that when the OSA-treated waxy maize was converted with a mixture of alpha amylase and beta amylase, a low molecular weight peak (800) was observed. However, the low normalized area of the peaks detected indicates that most of the sample is excluded and not detected. The low molecular weight material was estimated to be about 12% based on the weight of the final product.

Example 9

This example shows the preparation of another enzyme-converted, highly acetylated starch. It was prepared using the single phase, high solids process.

An acetylated waxy maize starch (1.05 D.S.) was converted by alpha amylase, as described in Example 1, using 1,000 g of starch, 40% total water, and 1 ml each of BAN 120 L and TERMAMYL. The starch began to liquify at about 80° C. A watery liquid product was observed in the Ross Mixer as the temperature increased to 95–98° C. After the mixture was held at 95–98° C. for 2 hours, a hardened rock-like material formed in the Ross Mixer.

The unconverted acetylated waxy maize (1.05 D.S.) cannot be detected by GPC, probably because of its high molecular weight or great hydrodynamic volume in the DMSO mobile phase. The GPC molecular weight profile of this converted acetylated waxy maize (1.05 D.S.) showed multiple peaks. Its Brookfield viscosity (5% solids in DMSO, Spindle #4, 100 rpm) was 56 cps, whereas the Brookfield viscosity of the non-converted acetylated waxy maize at the same concentration was 2,480 cps (5% solids, Spindle #4, 20 rpm). This significant viscosity reduction indicates that the acetylated waxy maize has been hydrolyzed and depolymerized even though it had a DS of 1.05.

Example 10

This example describes the enzyme conversion of a pregelatinized granular starch.

A ten gallon jacketed tank with a gate agitator is charged with 33 pounds of a chemically modified, pregelatinized granular corn starch. The starch is made by reacting granular corn starch with sufficient propylene oxide to give a D.S. of about 0.05 and subsequently predispersing the hydroxypropylated granular starch by the spray drying using the process of U.S. Pat. No. 4,280,851. To the starch powder is added 30 grams of TERMAMYL 120 L diluted in 5.6 pounds water for a starting solids of about 75%. A minimum of mixing is used to distribute the added water and enzyme into the starch. If necessary, the pH is adjusted to 6.5. The agitation is stopped and steam is injected into the mixture to raise the temperature to 90° C. After the mixture reaches 90° C., agitation is restarted, the injection of steam is stopped, and the temperature is maintained at 90–95° C. with jacket heating. Within one hour the mixture should be converted to a chemically modified maltodextrin syrup of DE 10-19. This syrup should be clear to translucent when hot but may set to a soft gel over time after cooling.

Example 11

This example shows the use of four maltodextrins made by the single phase conversion process in a high solids paper coating formulation.

The starches were an alpha-amylase-converted waxy maize at 10.2% solids, an alpha-amylase-converted cationic waxy maize containing 3-chloro-2-hydroxypropyl trimethylammonium chloride groups (D.S. 0.04) at 71.2% solids, an alpha-amylase-converted hydroxyprbpylated waxy maize (D.S. 0.16) at 60.7% solids, and an alpha-amylase-converted octenylsuccinate waxy maize (D.S. 0.02) at 57.8% solids.

The starches were evaluated at 66%, 64%, and 62% solids in coatings which contained an acetate/acrylate latex (RESYN® 1151) at starch to latex binder ratios of 12:4 and 8:8. The viscosity of each maltodextrin was adjusted to match that of the control which was PENFORD GUM 280 (an ethylated 80 W. F. corn starch commonly used in paper coating applications).

All coatings were applied to alkaline basestock paper at 7 lbs./3000 ft² coat weight. The samples were oven dried at 260° F. for 20 seconds and then supercalendered (140° F., 3000 psi, 1 nip). Samples were tested for 75° Hunter gloss, TAPPI brightness, Parker Print smoothness, IGT pick strength, and NPA % ink transfer. See data sheet for more details. The results are shown in the following table.

Coated Sheet Testing Results

|  | Control | Unmodified Alpha Amylase Converted | Cationic Alpha Amylase Converted | PO Alpha Amylase Converted | OSA Alpha Amylase Converted |
|---|---|---|---|---|---|
|  | 12:4 | 12:4 | 12:4 | 12:4 | 12:4 |
| Hunter Gloss | 66.4 | 64.5 | 66.3 | 66.4 | 66.0 |
| TAPPI Brightness | 85.4 | 85.5 | 85.4 | 85.5 | 85.7 |
| Parker Print Smoothness | 2.6 | 2.8 | 2.9 | 2.8 | 2.7 |
|  | 2.1 | 2.2 | 2.2 | 2.1 | 2.1 |
| IGT Pick (#3, 5 m/s, 50 kgf) | 295 | 250 | 272 | 242 | 228 |
| NPA -% Ink Transfer | 21.7 | 34.3 | 35.2 | 30.5 | 28.0 |
|  | 8:8 | 8:8 | 8:8 | 8:8 | 8:8 |
| Hunter Gloss | 67.2 | 68.6 | 67.8 | 68.2 | 68.5 |
| TAPPI Brightness | 85.3 | 85.7 | 85.5 | 85.3 | 85.5 |
| Parker Print Smoothness | 2.8 | 2.8 | 3.0 | 2.9 | 3.0 |
|  | 2.2 | 2.3 | 2.3 | 2.3 | 2.2 |
| IGT Pick (#3, 5 m/s, 50 kgf) | 310 | 173 | 213 | 181 | 181 |
| NPA -% Ink Transfer | 25.4 | 31.8 | 35.1 | 31.4 | 28.0 |

All samples except for the cationic sample showed equivalent rheology to the control even at higher coating solids. Gloss, brightness, and smoothness were equivalent to the control. IGT Pick was equal or lower. Ink receptivity was improved.

Example 12

This example shows the use of single phase enzyme-converted starches in four food systems where standard, commercially available maltodextrins are typically used.

The first three applications are areas where high solids/ low viscosity relationships, a property typical of conventional maltodextrins, are needed. They include use as a cereal tackifier where adhesion, tack, and film-forming properties are required, use in a frozen desert as a fat replacer and stabilizer, and use in an emulsion system as a emulsifier/encapsulating agent. A high viscosity, single phase, enzyme-converted starch is used in a coffee creamer system to demonstrate utility beyond the conventional maltodextrin range.

| Part A - Cereal Tackifiers<br>The single phase enzyme-converted starches evaluated are shown below ||||||
| --- | --- | --- | --- | --- |
| Waxy Maize Starch | Enzyme Type/Amt. | Process* Time/Temp./% g Solids | Reducing Sugar DE | Degree of Substitution |
| Unmodified | TERMAMYL 120L/0.2% | 110 minutes/ 95 ± 2° C./72%-FP Solids | 23.1 | — |
| Hydroxypropylated (D.S.) | TERMAMYL 120L/0.2% | 110 minutes/ 95 ± 2° C./72%-FP Solids | 15.5 | 0.16 |
| Hydroxypropylated (D.S.) | TERMAMYL 120L/0.2% | 110 minutes/ 95 ± 2° C./72%-FP Solids | 15.7 | 0.05 |
| Unmodified | TERMAMYL 120L/0.2% | 90 minutes/ 97 ± 2° C./68%-FP Solids | 23.0 | — |
| Crosslinked Hydroxypropylated (0.007% POCl$_3$) | TERMAMYL 120L/0.2% | 90 minutes/ 97 ± 2° C./68%-FP Solids | 15.8 | 0.08 |

*FP is final product solids.
**POCl$_3$ is phosphorus oxychloride.

The samples were recovered in liquid form and were diluted to 30% solids for application testing. The adhesion and tackiness tests used to screen and qualify samples for cereal/snack applications are as follows:

Adhesion Test

The Saltine crackers were weighed, brushed with a solution of the enzyme-converted starch at 30% solids onto the top surface of the cracker, and then weighed. Dried apple bits were dropped onto the wet glaze. Excess bits were shaken off and the coated crackers were weighed, dried in an oven for 10 minutes at 107° C. (225° F.), and cooled to room temperature. Any loose apple bits were gently brushed off and the bits were weighed. The weight was calculated. The % loss was calculated.

Tackiness

A subjective test was done by placing a drop of solution between the fingers and observing the stickiness and strand formation as it dried.

The results are shown below:

| Waxy Maize Converted | Apple Bits %-Loss | Apple Bits %-Loss | Tackiness |
| --- | --- | --- | --- |
| Unmodified | 17.80 | — | — |
| Hydroxy-propylated (0.05 D.S.) | 19.99 | — | — |
| Hydroxy propylated (0.16 D.S.) | 15.83 | — | — |
| Unmodified | — | 28.49 | poor |
| Hydroxy-propylated and crosslinked (0.08 D.S.) 0.007% POCl$_3$ | — | 29.87 | poor |
| Comparative Maltodextrins ||||
| 10 DE Maltodextrin | 25.92 | 30.83 | none |
| 24 DE Maltodextrin | 29.21 | — | — |
| 42 DE Maltodextrin | 31.48 | — | — |

The results show that all of the single phase converted products which have reducing sugar values between 15.7–23.1%, outperform the 10–42 DE maltodextrins as cereal tackifiers by having a lower percentage of apple bit loss and increased tackiness.

Part B—Ice Cream

A highly enzyme-converted tapioca starch prepared by the single phase process was tested in hard pack ice cream formulation as a combination filler, fat replacer, and stabilizer. It was compared with MALTRIN 100 (a 10 DE maltodextrin) from Grain Processing Corp. (Muscatine, Iowa) which is typically used in the industry at a 4% usage level.

The ice creams contained the following ingredients:

|  | 10 DE Maltodextrin | Enzyme-Converted Tapioca Starch Prepared By Single Phase Process |
| --- | --- | --- |
| Skim Milk | 67.35 | 64.05 |
| Cane Sugar | 14.75 | 14.75 |
| Heavy Cream | 0.00 | 0.00 |
| Corn Syrup - 36 DE | 6.50 | 6.50 |
| Non-Fat Dry Milk | 6.60 | 6.60 |
| Maltodextrin - 10 DE* | 4.00 | 0.00 |
| Single Phase, Enzyme-Converted Tapioca Starch | 0.00 | 7.30 |

|  | 10 DE Maltodextrin | Enzyme-Converted Tapioca Starch Prepared By Single Phase Process |
|---|---|---|
| Stabilizer** | 0.80 | 0.80 |

*MALTRIN 100 from Grain Processing Corp.
**SHEREX 302 from Quest.

Extra water was added to the ice cream formulation made with single phase, enzyme-converted tapioca starch to compensate for a slight reduction in the quantity of skim milk used.

The dry ingredients were fully dispersed into the liquid ingredients and wet-out in a blender/mixer apparatus (Breddo Likwifier, modified 8 gallon unit from American Ingredients Co., 18th and Kansas Avenue, Kansas City, Kans. 66119). The mixture was pasteurized in an indirect tubular heat exchanger (Micro Thermics, UHT/HTST lab-25 HV from Micro Thermics, Inc., 5024F Departure Drive, Raleigh, N.C. 27604) representing a HTST (high temperature, short time) process at 185–190° F. for 30 seconds. The pasteurized hot mixture was then homogenized in two stages at 500/2000 psi in Gaulin, model 15 MR-8TBA from Gaulin Inc., Evertt, Mass. 02149).

The homogenized mixture was cooled and frozen in a hard pack ice cream machine (Taylor, model 110-27 from Taylor Company, Rockton, Ill.) according to manufacturer's instructions. The Zahn cup viscosity measurement of the cold mixes before freezing were identical (10 DE maltodextrin—21 seconds/25 grams and single phase, enzyme-converted tapioca starch—28 seconds/25 grams). The overrun percentages were also identical at about 60%. When the melt down test was conducted, the results showed that the rate of melt down in the sample containing the 10 DE maltodextrin was slightly faster than the single phase sample.

A total of 28 panel members evaluated the ice cream in Duo-preference taste test. The panelist were asked to rank the samples on a 15 cm line scale based on these attributes (iciness, melt-away, creaminess, firmness and coldness). In addition, they were asked to select the sample they perceived as the best. Thirteen people picked the single phase, enzyme-converted tapioca sample and fifteen picked the 10 DE maltodextrin as the best. With regards to iciness, many people picked the single phase, enzyme-converted starch as more icy over the 10 DE maltodextrin. The majority of the panel members also picked the single phase, enzyme-converted tapioca starch to have slower meltaway. The single phase, enzyme-converted tapioca was not as creamy as the 10 DE maltodextrin. The single phase, enzyme-converted tapioca was also perceived as firmer than the 10 DE maltodextrin. The two products were identical in coldness in the mouth.

According to Table T12 on page 261 of the "Sensory Evaluation Techniques," one should accept the null hypothesis of no difference with 90% confidence if the number of correct responses is less than or equal to 14 out of 28 total responses. Our results obtained 13 out of 28 in favor of the single phase, enzyme-converted tapioca. Based on these results, the single phase, enzyme-converted tapioca was not significantly different compared with 10 DE maltodextrin. However, the single phase enzyme-converted tapioca sample had slower melt down and was firmer than the 10 DE maltodextrin. These are positive attributes that are crucial to major ice cream manufacturers.

Part C - Encapsulation of Flavor Emulsion
This example shows the efficacy of the single phase enzyme-converted starches in flavor emulsion systems

| Treatment/ Type of Conversion | Viscosity |
|---|---|
| OSA Waxy Maize/Alpha Amylase | Low |
| OSA Waxy Maize/Alpha/Beta Amylase | High |
| Conventional Maltodextrins | Low |
| Acid-Converted OSA-Treated Waxy Maize | High |

Low viscosity emulsions were made using the converted starch as a carrier. The carrier to flavor ratio was 80/20. The single phase alpha amylase-converted OSA waxy maize sample gave a much finer emulsion compared to Lodex 10 based on the particle size distribution. This was also reconfirmed by overnight distinct oil separation in the case of Lodex 10 instead of creaming in the case of the single phase alpha amylase-converted starch.

The data is summarized in the table below.

| Sample | Emulsion's Viscosity And Particle Size In Microns | | | Overnight Observation |
|---|---|---|---|---|
|  | Viscosity | Median | Mean |  |
| Single Phase OSA Waxy/Alpha | 40 cps | 2.267 | 7.460 | Creaming |
| LODEX-10 | 20 cps | 21.390 | 24.968 | Distinct Oil Layer |

The single phase alpha/beta amylase-converted OSA waxy maize was compared with an acid-converted OSA-treated waxy maize in a coffee-creamer (spray-dried starch/vegetable fat emulsion) application. The emulsions made with the single phase alpha/beta amylase-converted OSA waxy and the acid-converted OSA-treated waxy maize had similar particle size distributions and comparable emulsification properties. In hot coffee both samples showed moderate oiling off. The data are summarized in the table below:

| Sample | Viscosity | Emulsion's Viscosity And Particle Size In Microns | | | |
|---|---|---|---|---|---|
|  |  | Fresh | | Reconstituted | |
|  |  | Median | Mean | Median | Mean |
| Single Phase OSA Waxy/Alpha | 322 cps | 1.394 | 1.569 | 2.802 | 3.931 |
| Conventional Acid-Converted OSA-Treated Waxy Maize | 250 cps | 1.142 | 1.235 | 2.09 | 3.94 |

Example 13

This example shows the use of a fully converted, hydroxypropylated (PO) waxy maize and a partially converted, unmodified waxy maize, prepared by the high solids, single phase enzyme conversion process in a corrugating adhesive with and without added caustic. These fully solubilized adhesives were compared to a Stein-Hall type control (caustic dispersed carrier starch with suspended raw starches).

At room temperature, the 61% solids converted P.O. waxy maize and the 71% solids converted waxy maize had viscosities of 3000 cps. and >20,000 cps., respectively. When held in a boiling water bath, the materials thinned considerably. At 200° F., the 61% solids converted P.O. waxy maize had a 45 second viscosity as measured in the Stein-Hall cup. To maintain a high solids level and move the adhesive viscosity towards standard levels, the materials were heated prior to being poured in the glue pan.

The 61% solids P.O. waxy maize was evaluated on the corrugator using a standard gap setting of 0.012 in. The adhesive was unable to deliver bonded single face web at speeds above 50 ft./min. When the board was analyzed immediately off the corrugator, there was no evidence of fiber tear. It appeared that the adhesive had not penetrated the paper. Caustic was added to the adhesive to increase alkalinity and improve the adhesives bite into the paper. At 0.5% on the mass of the adhesive, the caustic made a significant difference and the adhesive was run at 175 ft./min.

The 71% partially dispersed, converted waxy maize was held at 88° C. (190° F.). Even at that temperature, the viscosity was approximately 2000 cps. To thin the adhesive and add bite, 0.5% caustic was added based on the total mass. At a gap of 0.012 in., the adhesive was able to produce single face web at speeds of 250 ft./min. Board was also produced at a top speed of 450 ft./min.

To compare this adhesive to Stein-Hall adhesives, 250 ft./min. runs were completed at gap settings of 0.008, 0.014, and 0.020 in. The bond strength vs. adhesive pick up were determined using the ICD procedure for pin strength analysis and the ICD enzyme test for pick up. All the experimental adhesives were held between 66 and 93° C. (150° F. and 200° F.). The specifications for the runs are shown below.

| No. 1 | Material: | 63% solids fully dispersed P.O. waxy |
|---|---|---|
| | Speed: | 50 ft./min. |
| | Caustic: | none |
| | Gap: | 0.012 |
| | Pick up: | 1.6 lb / MSF |
| | Bond: | 3.1 lb/lineal ft. |
| No. 2 | Material: | 63% solids fully dispersed P.O. waxy |
| | Speed: | 175 ft./min. |
| | Caustic: | 0.5% on total adhesive |
| | Gap: | 0.012 |
| | Pick up: | 1.6 lb / MSF |
| | Bond: | 4.3 lb/lineal ft. |
| No. 3 | Material: | 71% solids partially dispersed unmodified waxy |
| | Speed: | 250 ft./min. |
| | Caustic: | 0.5% on total adhesive |
| | Gap: | 0.008 |
| | Pick up: | 1.4 lb / MSF |
| | Bond: | 10.3 lb/lineal ft. |
| No. 4 | Material: | 71% solids partially dispersed unmodified waxy |
| | Speed: | 250 ft./min. |
| | Caustic: | 0.5% on total adhesive |
| | Gap: | 0.014 |
| | Pick up: | 5.0 lb / MSF |
| | Bond: | 28.0 lb/lineal ft. |
| No. 5 | Material: | 71% solids partially dispersed unmodified waxy |

-continued

| | |
|---|---|
| Speed: | 250 ft./min. |
| Caustic: | 0.5% on total adhesive |
| Gap: | 0.020 |
| Pick Up: | 9.9 lb / MSF |
| Bond: | 32.5 lb/lineal ft. |

One major weakness of both adhesives was the final bond strength given the adhesive pick up. An acceptable bond strength is considered to be 50 lb/lineal ft. Even with 9.9 lb/MSF, the better performing 71% solids converted waxy maize was unable to surpass the minimum standard. On the same paper, a Stein-Hall adhesive is capable of achieving a bond strength of 50 lb/lineal ft. using 1.5 lb/MSF. The board produced by the 63% solids converted P.O. waxy maize had virtually no fiber tear. There was a maximum of 25% fiber tear even for the highest pick up of the 71% solids waxy. The partially converted material probably had some higher molecular weight polymer chains which could be the reason for the improved bond strengths.

Example 14

This example describes the preparation of a layflat laminating adhesive.

To a clean, dry tank 45.52 parts of an OSA-modified waxy maize (3% OSA) is added followed by a premix of 7.25 parts of water and 0.09 parts of TERMAMYL. Mixing at 30 rpm is carried out while the premix is added in a slow, steady steam. Mixing is continued until the mixture is uniformly damp and then the agitator is shut down. The mixture is heated with live steam and jacketed steam to 180–200° F. for 30 minutes or until liquid forms uniformly around the tank and at the steam lines. Then 9.00 parts of water are added and the agitation is restarted at 30 rpm while continuing to heat. The temperature is held at 200–210° F. while mixing. When the product clarifies and is smooth, the viscosity and solids are tested. When the test results are recorded, then 0.05 parts of 85% phosphoric acid are added.

The pH is adjusted to 3.5 with additional acid if needed to end the enzyme activity. The heat is turned off and 12.90 parts of sodium nitrate are added. The mixture is cooled to below 140° F. and 0.30 parts of defoamer, 11.84 parts of magnesium chloride hexahydrate, 12.90 parts of calcium chloride, and 0.15 parts of preservative are added.

The Brookfield viscosity is adjusted to 2000–5000 cps on by adding water. The adhesive is expected to demonstrate excellent lay-flat, high solids, good adhesion, and superior stability.

Example 15

This example describes the preparation of a case and carton sealing adhesive.

To a clean, dry tank are added 43.52 parts of a cationic waxy maize starch containing diethylamino chloride groups (0.04 D.S.) and then a premix of 6.95 parts of water and 0.09 parts of TERMAMYL are added.

Mixing at 30 rpm is carried out while the premix is being added in a slow, steady steam. Mixing is continued until the starch is uniformly damp and then the agitator is shut down. The mixture is heated with live steam and jacketed steam to 180–200° F. for 30 minutes or until liquid forms uniformly around the tank and at the steam lines. Then 6.94 parts of water are added. Agitation is restarted at 30 rpm while heating is continued. The mixture is held at 200–210° F.

while mixing. When the product clarifies and is smooth, viscosity and solids are tested. When test results are recorded, then 0.05 parts of 85% phosphoric acid are added. The pH is adjusted to 3.5 with additional acid if needed to end the enzyme activity.

The heat is turned off and then 6.5 parts of water, 35.5 parts of polyvinyl acetate, 0.3 parts of a defoamer, and 0.15 parts of preservatives are added.

The Brookfield viscosity is adjusted to 500–5000 cps by dilution with water. This adhesive is designed for fast drying, high tack, and excellent adhesion.

Example 16

This example describes the preparation of a grocery bag adhesive.

The procedure described in Example 12 is used to enzyme-convert 43.52 parts of hydroxypropylated waxy maize (D.S. 0.09). The premix consists of 6.95 parts of water and 0.09 parts of TERMAMYL. The amount of water added after the starch liquified is 6.94 parts. After the enzyme is deactivated and the heat is turned off, 42.00 parts of water, 0.15 parts of preservative, and 0.30 parts of defoamer are added. The solution is diluted to a 1500–5000 cps Brookfield viscosity. The adhesive should produce faster set, higher solids, stronger adhesion as well as minimal wrinkling compared to a standard bag adhesive.

Example 17

This example describes the preparation of a tube-winding adhesive.

The procedure used in Example 12 is used to enzyme convert 43.52 parts of a hydroxypropylated fluidity waxy maize (35WF, D.S. 0.16). The premix consists of 6.95 parts of water and 0.09 parts of TERMAMYL. After the starch is liquified, 6.94 parts of water are added. After the enzyme is deactivated and the heat is turned off, 1.10 parts of 25% sodium hydroxide, 30.0 parts of 5 mole borax, 8.0 parts of aluminum silicate, 0.30 parts of defoamer, and 0.15 parts of preservative are added.

The Brookfield viscosity is adjusted to 2000–10,000 cps by dilution with water. This adhesive is designed for superior tack and very fast set speed with minimal puckering and excellent adhesion.

Example 18

This example describes the preparation of an envelope seam adhesive.

The procedure described in Example 12 is used to enzyme convert 43.52 parts of corn starch. The premix consists of 6.95 parts of water and 0.09 parts of TERMAMYL. The amount of water added after the starch liquifies is 6.94 parts. After the test results are recorded, 0.03 parts of 20 Baume' hydrochloric acid are added. After the heat is turned off and the solution is cooled, 32 parts of magnesium chloride hexahydrate, 10.0 parts of water, 0.30 parts of defoamer, and 0.15 parts of preservative are added.

The Brookfield viscosity is adjusted to 200–8000 cps by dilution with water. This adhesive should demonstrate high tabbing resistance due to the elevated solids, excellent rheology for clean machining, good adhesion, and light color which will eliminate discoloration of paper seams.

Example 19

This example describes the preparation of a label wrap adhesive.

Using the procedure described in Example 12, 43.52 parts of waxy maize starch is enzyme-converted. The premix consists of 6.95 parts of water and 0.09 parts of TERMAMYL. After the starch is liquified 6.94 parts of water are added. To stop the enzyme activity 0.03 parts of 20 Baume' hydrochloric acid are added. After the cooling, 20.0 parts of sodium nitrate, 15.0 parts of urea, 0.30 parts of defoamer, 0.15 parts of preservative, and 7.00 parts of water are added.

The Brookfield viscosity is adjusted to 10,000–100,000 cps (which depends on the machinery to be used) using water as the diluent. This adhesive is expected to produce less paper wrinkling, have high tack, good adhesion, and light color.

Now that the preferred embodiments of the invention have been described in detail, various modifications and improvements thereon will become readily apparent to those skilled in the art. Accordingly, the spirit and scope of the present invention are to be limited only by the appended claims and not by the following specification.

What is claimed:

1. An enzyme conversion process for preparing a liquefied, enzyme-converted starch, which comprises the steps of:

heating a composition comprising a modified or an unmodified, pregelatinized or ungelatinized granular starch, water, and one or more starch-hydrolyzing enzyme(s), wherein said composition is a single phase, high solids, powdered mixture without a free water phase, to about the optimum temperature for said enzyme(s) while maintaining a substantially constant moisture content in said composition; and allowing the starch hydrolyzing enzyme(s) to hydrolyze and liquefy the starch in said composition.

2. The process of claim 1, wherein the amount of water added in step (a) is sufficient to give a total water content of about 15% to about 40%.

3. The process of claim 2, wherein the water content is about 30% to about 35%.

4. The process of claim 1, wherein the starch-hydrolyzing enzyme is selected from the group consisting of an enzyme which hydrolyzes the 1–4→ linkages of the starch, an enzyme which hydrolyzes the 1,6→ linkages of the starch, an enzyme which hydrolyzes both the 1,4→ and the 1,6→ linkages of the starch, and mixtures thereof.

5. The process of claim 4, wherein the starch-hydrolyzing enzyme is selected from the group consisting of alpha amylase, beta amylase, glucoamylase, pullulanase, isoamylase and mixtures thereof.

6. The process of claim 1, wherein the enzyme is activated by adjusting the pH of a buffer to the optimum pH of the enzyme.

7. The process of claim 1, wherein the powdered mixture is directly heated, indirectly heated, or directly and indirectly heated.

8. The process of claim 7, wherein the powdered mixture is directly heated by injecting steam.

9. The process of claim 1, wherein the powdered mixture of step (a) contains an activating salt.

10. The process of claim 1, further comprising the step of inactivating the enzyme in the mixture of step (c) by reducing the pH, by increasing the temperature, by adding an inhibiting salt, by reducing the pH and increasing the temperature, by reducing the pH and adding an inhibiting salt, or by reducing the pH, increasing the temperature, and adding an inhibiting salt.

11. The process of claim 1, wherein the starch-hydrolyzing enzyme is selected from the group consisting of a bacterial alpha amylase which has an optimum temperature of about 65 to about 105° C. and pH of about 5.8 to about 6.5, a fungal amylase which has an optimum temperature of about 54 to about 56° C. and pH of about 4.9 to about 5.3, a glucoamylase which has an optimum temperature of about 58 to about 60° C. and pH of about 4 to about 5, a malt beta amylase which and an optimum temperature of about 45 to about 60° C. and pH of about 4.9 to about 5.3, a mixture of a fungal alpha amylase and a glucoamylase which has an optimum temperature of about 45 to about 65° C. and pH of about 4.9 to about 5.3, a pullulanase which has an optimum temperature of about 45 to about 70° C. and pH of about 4.5 to about 5.5 and an isoamylase which has an optimum temperature of about 25 to about 50° C. and pH of about 3.5 to 5.5.

12. The process of claim 1, wherein the starch of step (a) is a non-pregelatinized granular starch.

13. The process of claim 1, wherein the starch of step (a) is a pregelatinized granular starch.

14. The process of claim 1, wherein the starch of step (a) is a dispersed non-cold-water-soluble starch powder.

15. The process of claim 1, wherein the starch of step (a) is a chemically modified starch or a physically modified starch.

16. The process of claim 15, wherein the chemically modified starch of step (a) is a derivatized starch, a crosslinked starch, or a converted starch.

17. The process of claim 15, wherein the physically modified starch is a heat treated starch.

18. The process of claim 1, wherein the liquefied starch comprises a syrup optionally containing granular converted starch or a mixture of granular converted starch and unconverted, ungelatinized granular starch.

19. The process of claim 18, wherein the syrup has a solids content of about 60–80 wt. %.

20. The process of claim 19, wherein the solids content is about 70–75%.

21. A powdered enzyme-converted starch recovered by drying the syrup of claim 18.

22. A process for preparing an enzyme-converted granular starch, which comprises the steps of:

heating a composition comprising a modified or an unmodified, pregelatinized or ungenatinized granular starch, an alpha amylase, and water to provide about 15 to about 35% total water by weight, wherein said composition is a single phase, high solids, powdered mixture without a free water phase, to about the optimum temperature for said alpha amylase while maintaining a substantially constant moisture content in said composition; and allowing the alpha amylase to partially hydrolyze the starch in said composition.

23. A process for preparing a granular, enzyme-converted starch, which comprises the steps of:

heating a composition comprising a modified or an unmodified pregelatinized or ungelatinized granular starch, at least one enzyme selected from the group consisting of beta amylase, glucoamylase, pullulanase, and isoamylase, alpha amylase, and water, wherein said composition is a single phase, high solids, powdered mixture without a free water phase, to about the optimum temperature for said enzyme or enzyme mixture while maintaining a substantially constant moisture content in said composition; and allowing the enzyme or enzyme mixture to partially hydrolyze the starch in said composition.

24. The process of claim 23, wherein the enzyme is glucoamylase.

* * * * *